(12) United States Patent
Zimmon

(10) Patent No.: US 6,468,227 B2
(45) Date of Patent: *Oct. 22, 2002

(54) DEVICE FOR PERFORMING A MEDICAL PROCEDURE

(75) Inventor: David S. Zimmon, Port Washington, NY (US)

(73) Assignee: Zimmon Science Corporation, Port Washington, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/810,100

(22) Filed: Mar. 16, 2001

(65) Prior Publication Data

US 2001/0056248 A1 Dec. 27, 2001

Related U.S. Application Data

(60) Provisional application No. 60/190,234, filed on Mar. 17, 2000.

(51) Int. Cl.[7] .............................................. A61B 10/00
(52) U.S. Cl. ........................ 600/564; 606/159; 606/170
(58) Field of Search ................................. 600/564, 565, 600/566, 567; 604/22, 508, 96.01; 606/45–48, 159, 167, 170, 194

(56) References Cited

U.S. PATENT DOCUMENTS

| | | | | |
|---|---|---|---|---|
| 4,765,332 A | * | 8/1988 | Fischell et al. | 606/159 |
| 5,085,659 A | * | 2/1992 | Rydell | 606/47 |
| 5,366,463 A | * | 11/1994 | Ryan | 606/159 |
| 5,653,240 A | | 8/1997 | Zimmon | 600/486 |
| 5,685,320 A | * | 11/1997 | Zimmon et al. | 600/567 |
| 5,980,468 A | | 11/1999 | Zimmon | 600/567 |
| 6,050,955 A | * | 4/2000 | Bryan et al. | 600/564 |

* cited by examiner

*Primary Examiner*—Kevin Shaver
*Assistant Examiner*—Charles Marmor, II
(74) *Attorney, Agent, or Firm*—Collard & Roe, P.C.

(57) ABSTRACT

An apparatus and method for performing a medical procedure comprising an elongated shaft having an aperture extending longitudinally therethrough. An actuator tube is positioned within the shaft and a guide wire extends through the tube. A head is attached at one end of the shaft by the guide wire. A specimen is cut by a blade disposed on either the shaft or the head. The device is used to enlarge a lumen that has been occluded with diseased or stenotic tissue.

29 Claims, 4 Drawing Sheets

DEVICE FOR PERFORMING A MEDICAL PROCEDURE

This application claims the benefit of provisional application No. 60/190,234 filed on Mar. 17, 2000.

BACKGROUND OF THE INVENTION

1. Field of the Invention

The invention relates to a method and device for removal of diseased tissue for disposal or analysis.

2. The Prior Art

A Lateral Biopsy Device is shown in U.S. Pat. No. 5,653,240 and a device and method for Serial Collection, Storage and Processing is Described in U.S. Pat. No. 5,980,468, both which are hereby incorporated reference. These references disclose techniques for removing tissue by cutting, coring and scraping. The tissue is cut, captured, stored and removed for analysis or disposal from sites deep within body cavities. The tissue is taken from approached long paths to organ lumens as in the gastrointestinal, pulmonary, urological, gynecological, neurological or vascular systems. These methods are useful in many medical applications with modifications appropriate to the specific disease and diagnostic or therapeutic purpose.

SUMMARY OF THE INVENTION

An object of the present invention is to provide for removal or ablation of diseased tissue for restoring a stenotic or occluded lumen to patency. In the process of the present invention, the diseased tissue is captured within a cone tip or a tube shaft of a lateral biopsy device and retrieved for disposal or analysis. This allows for analysis of serial specimens of tissue to determine the completeness of removal as in ablation of a malignancy or removal of plaque in blood vessels. When removing occluding plaque within a blood vessel, storage and retrieval prevents distal embolization of fragments that would occlude smaller distal blood vessels.

Removal of obstructing tissue within a blood vessel lumen requires traversing the vascular lumen leading to the obstruction, passing through the obstruction and coring or scraping the obstructing material into the head or shaft of the lateral biopsy. Traversing a vascular lumen over a guide wire is a standard medical technique. The wire guided lateral biopsy is modified according to the invention by replacing the filiform leader and wire actuator with a central plastic tube attached to the perforated cone blade tip that passes over the previously inserted guide wire. The cone blade tip must pass the obstruction as a dilator or be compressed to traverse the stenosis and expand to serve as a cutting device or an anvil for a shaft blade. Many obstructing lesions are elastic. They compress to allow dilator passage only to reexpand and obstruct. For these lesions the cone tip serves as both a dilator and a cutting device or an anvil. In more rigid lesions, as in peripheral vascular obstructions, the cone dilator must be compressible with a flower petal configuration. The compressive force of the rigid lesion and the catheter shaft traversing the guide wire closes the petals of the cone traversing and dilating the stenosis. The catheter tube shaft blade is then advanced to meet the cone and cores off the obstructing tissue into the shaft.

Alternatively, the backward facing cone blade may be pulled back with the central tube and the obstructing tissue captured within the cone tip. For long lesions, as in peripheral arteries, a shaft blade with shaft capture provides a large storage space for cored tissue. A preferred embodiment would have a diameter range of 3 to 10 mm. For short lesions, capture in the tip is sufficient and allows a smaller more flexible lateral biopsy device suitable for smaller arteries 2–3 mm in diameter, such as in the heart. This would be particularly useful for eccentric soft lesions in the coronary arteries. A preferred diameter for these lesions is 2 to 4 mm.

For eccentric lesions, the cone blade is modified to have the cutting blade in a specific quadrant allowing removal of the visible lesion with protection of the opposite side of the lumen. This is accomplished by using a radiolucent plastic tip with a radiopaque blade inserted into a segment of the cone. More rigid calcified tissue can be removed by adapting the coring surfaces through a rotating saw blade or abrasive hardened surface. Either rotational or vibrational forces are applied to the blade through a central tube wire lumen of the cone blade tip or by rotating the tube shaft of the shaft blade.

In another preferred embodiment, the cutting surface is in the shaft and the cone tip serves to prevent downstream loss of cored material until the tip and shaft close. To close the apparatus, the apposition of the shaft and tip capture the free material in the shaft lumen preventing loss while the instrument is withdrawn. This is an important feature to prevent distal embolization of the cored material in the vascular system.

Removal or ablation of neoplastic tissue by cutting, coring or scraping serves to restore a stenosed lumen and remove debris. Completeness of the removal, i.e. excisional biopsy, as determined by microscopical study of the tissue specimens, obviates the need for other therapy such as traditional surgical excision, radiation or chemotherapy. Early neoplastic lesions may have a long latent period before becoming invasive, symptomatic or metastatic. Therefore, as detection of early neoplastic lesions increases, the need for low risk minimally invasive, cost effective removal increases. The bile duct, pancreatic duct, bronchi and ureter are prone to neoplastic transformation. These lumens are difficult to access and treat by traditional surgical methods but easily accessed by endoscopy. Neoplasms in these areas are ideal for biopsy, excision, or debulking by the methods described here. Additionally, ablation of tissue and sealing of bleeding points would be accomplished by electrical heating or coagulation of the tissue surface performed by passing the appropriate electrical current to the metal cone tip or shaft blade.

After the lumen is enlarged to the diameter of the first instrument and that instrument is removed, leaving the wire guide in place, serial instruments of larger diameter are passed over the wire guide to further enlarge the lumen. Serial instrument passes allow progressive enlargement of the lumen. For example, a blood vessel or bile duct 10 mm in diameter with a 90% obstruction has a 1 mm lumen that allows passage of a 1 mm wire. Passage of a 2 mm diameter coring instrument would be followed serially by a 4 mm, then 6 mm, 8 mm and 10 mm instruments until the original lumen of 10 mm was restored. Each successive enlargement of the lumen would allow passage of a stiffer more efficient coring device followed by exchange for a stiffer wire guide to provide the necessary increase in coring force required by the larger surface area cored. Each pass traverses a path prepared by its predecessor. This is an advantage of the present invention as compared to balloon dilation or passage of concentric dilators that dilate without tissue removal. In these techniques, although the lumen is restored, in part, a large mass of unwanted tissue is displaced laterally rather than removed. Tissue recoil may close the lumen after dilation or the blood vessel rupture. The unwanted tissue may contribute to the frequent blood vessel restenosis. In cancer, the bulk of a compressed residual tumor may cause restenosis and limits the effectiveness of chemotherapy or radiation.

Monitoring is facilitated by radiography with injection of radiopaque contrast or other imaging techniques using the lumen leading to the space between the tip and shaft or the wire guide lumen. In the larger instruments a secondary lumen for contrast injection could be added to the shaft. The injection lumen also allows fluid sampling and pressure measurement.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
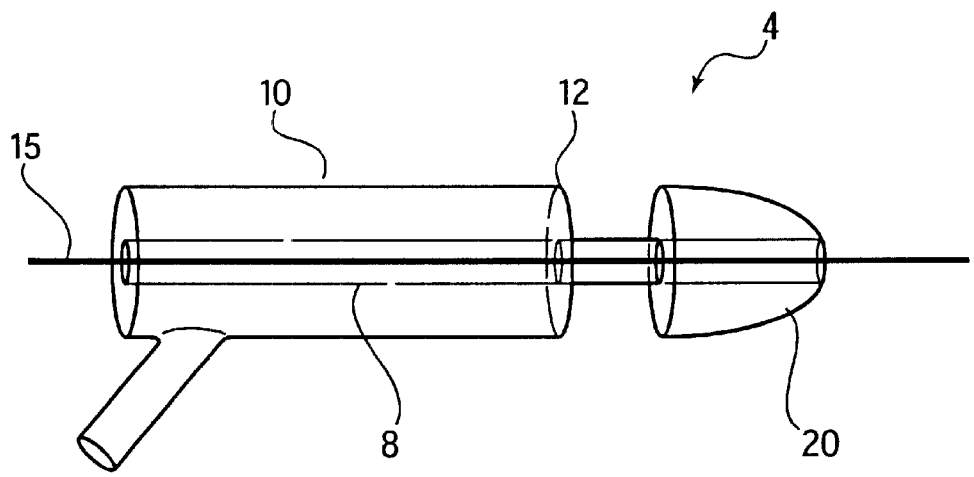
FIG. 1 shows a wire guided lateral apparatus having the cutting blade on the shaft according to the invention.

Referring now in detail to the drawings and, in particular, with reference to FIGS. 1 through 5, there is illustrated several embodiments of the device according to the invention, which permits serial specimen collection, storage and processing. As shown in FIG. 1, a biopsy device 4 contains a blade 12 disposed on an elongated shaft 10. An aperture extends through shaft 10 allowing an actuator tube 8 to extend therethrough. A wire guide 15 extends through actuator tube 8 and attaches to a cone-shaped head 20. Blade 12 is disposed on shaft 10, as shown in FIG. 1 or on head 20, seen in FIG. 2. Biopsy width is constrained by wire guide 15 to approximately 50% of the diameter of cutting blade 12. Within areas of narrowing, specimen 11 is forced into the cutting chamber and cannot escape except into either the receptacle head or shaft. These external constraints, combined with a conical packing shaft 18 within the head 20 shown in FIG. 6, provide the force to align, pack, and maintain specimen position as well as prevent loss of the specimen 11 when shaft 10 and head 20 are drawn apart for additional procedures.

When the device according to the invention is used within an unconstrained space, the force to align, pack, and store the tissue specimens must be provided by the instrument itself. In this circumstance, specimen size is important and a minimum specimen length of twice the blade diameter is assumed to align specimens within the storage space and prevent mixing. This is provided by calibrating shaft movement to that minimum distance. Packing of specimen 11 into shaft 10 and prevention of loss is accomplished by conical packing shaft 18 attached to cutting head 20 that extends into shaft 10 so that packed specimens are constrained.

Figure 2:
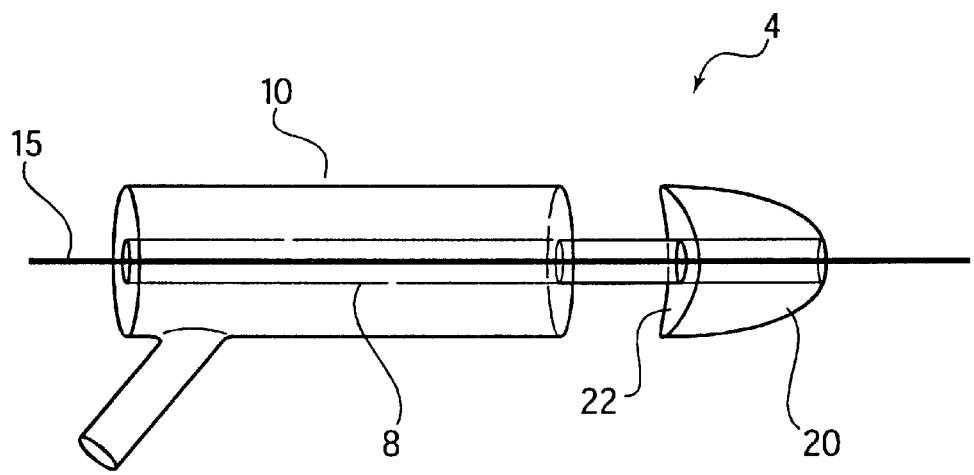
FIG. 2 shows a wire guide lateral apparatus having the cutting blade on a part of the cone head.
Figure 3A:
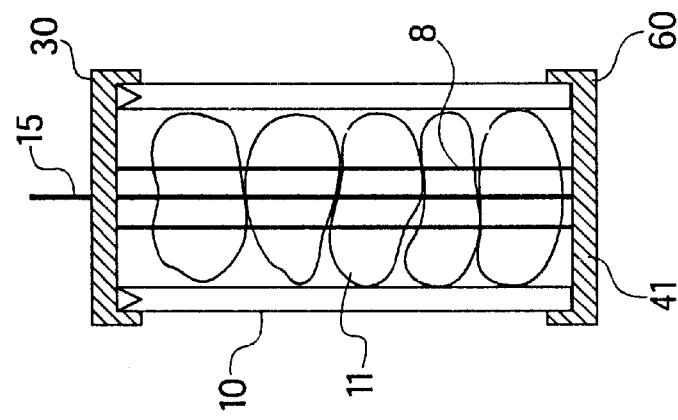
FIG. 3A shows the apparatus with two caps.
Figure 3:
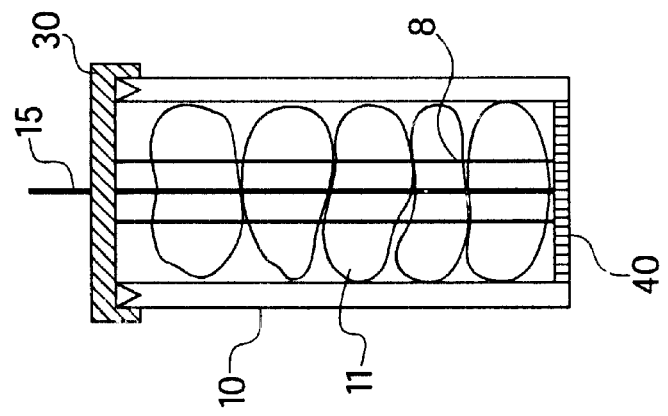
FIG. 3 shows the apparatus when cut and sealed for analysis.

The procedure described above allows the operator to collect and store the specimens in the sequence of acquisition, and allows hands-off processing of the specimens without loss of sequence. The device according to the invention provides for either a cutting head or a cutting shaft. Either of these parts may be used as the receptacle for serial specimens that may then be processed in situ. Each option has distinct advantages and disadvantages that will be made clear by the following:

FIG. 3 shows storage of specimens 11 in the shaft 10, which is a catheter. Shaft storage has the advantage of great storage space in relation to the length of the cutting head without altering operating characteristics of the biopsy device. This option permits retrieval of many samples and a large specimen volume using device diameters of 5F or smaller where head length is limited to 3 times shaft diameter by the need to traverse narrow tortuous pathways. FIG. 1 shows the cutting blade 12 disposed on the shaft 10. As shown in FIG. 2, the cutting blade is on the head, and collection of specimens 11 proceeds by moving blade 22 by tension on wire 15. Blade 22 cuts specimen 11, which is then drawn down into shaft 10. Packing head 18 shown in FIG. 6 serves to compress specimens 11 further into shaft 10. Wire 15 also compresses specimens 11 within shaft 10.

A stopper 40, shown in FIG. 3, is placed within shaft 10 and connected to wire 15. Stopper 40 is preferably perforated and serves as an end point to the storage chamber formed by shaft 10.

After the desired number of specimens 11 has been collected and the instrument removed from the patient's body, head 20 is removed from shaft 10. Wire 15 is cut and led through a perforated cap 30, which is placed over the open end of shaft 10, as shown in FIG. 3. Wire 15 is then pulled from cap 30 to raise stopper 40 and compress specimens 11 within shaft 10.

If the initial distance between stopper 40 and the end of shaft 10 where cap 30 is placed is known, the length of the shaft containing the specimens to be processed can be determined by measuring the length of wire outside the cap after the wire is pulled through the cap. Shaft 10 can then be cut to this length to create a compact processing cassette for specimens 11. Cap 30 and stopper 40 allow for exposure of specimens 11 during storage and processing. Alternatively, two caps 30 and 40 can be used as shown in FIG. 3A.

In FIG. 2, cutting blade 22 cuts specimens 11 when head 20 is guided by wire 15. If stored in head 20, head 20 is hollow in shape and serves as the storage chamber for specimens 11. Blade 22 can extend around the entire circumference of head 20, or can extend around a portion of the head's circumference. If blade 22 is only on a portion of the circumference, the remaining edge is recessed allowing for easier sliding over lesions.

Cutting head 20 is a cylindrical space made of metal or plastic with a proximal facing blade. The headspace has a direct relationship to its diameter, length and the size of the sample. The head diameter must conform to the shaft diameter. Head length is limited by the rigidity produced by head length that impedes maneuverability of the device.

Head length must be limited, generally, to between 2 and 10 times shaft diameter to allow easy passage of the device around curves in the endoscope or passage that is to be traversed. The possibility of special cases remains.

Head 20 is preferably perforated to allow for packing of the specimens 11 within head 20 by injecting fluid through shaft 10 into head 20. The fluid pressure causes specimens 11 to be compressed into head 20 and the fluid can then escape through perforated head 20.

When the desired number of specimens 11 have been collected in head 20, wire 15 is cut and cap 30 is placed over the opening in head 20 to enclose specimens 11. Cap 30 is preferably perforated to allow the addition of fixative to specimens 11. Alternatively, a tube of plastic screen can be placed within the hollow head 20, which is then closed on either end with a packing disc and removal plate. The screen can then be removed from head 20 for further processing and storage of specimens 11.

Figure 4:
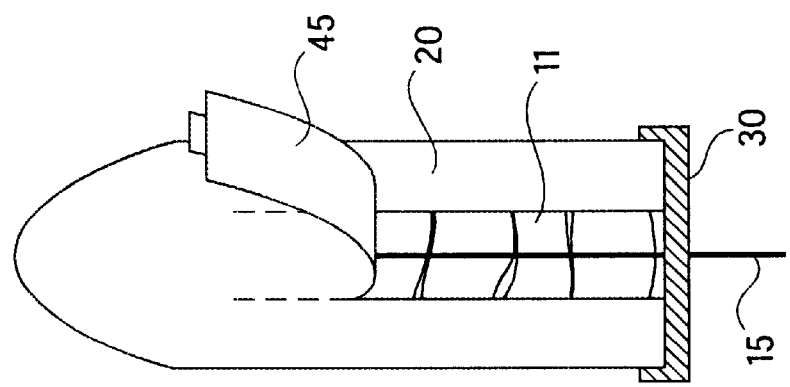
FIG. 4 shows the cone head having a perforated flap.

As shown in FIG. 4, head 20 preferably has a perforated flap 45 formed therein, which can be peeled open to release specimens 11 from head 20 for further processing.

Figure 5:
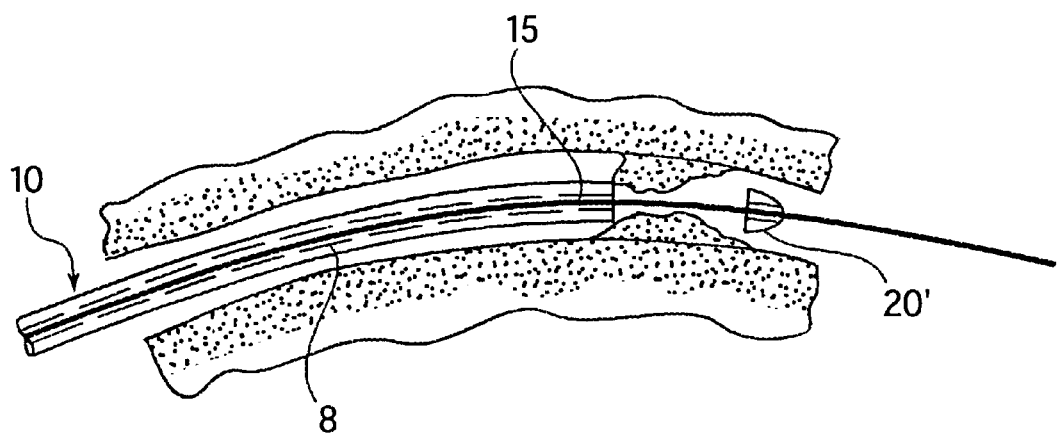
FIG. 5 shows the wire guided lateral apparatus having a compressible petal-shaped head and inserted into a lumen.
Figure 6:
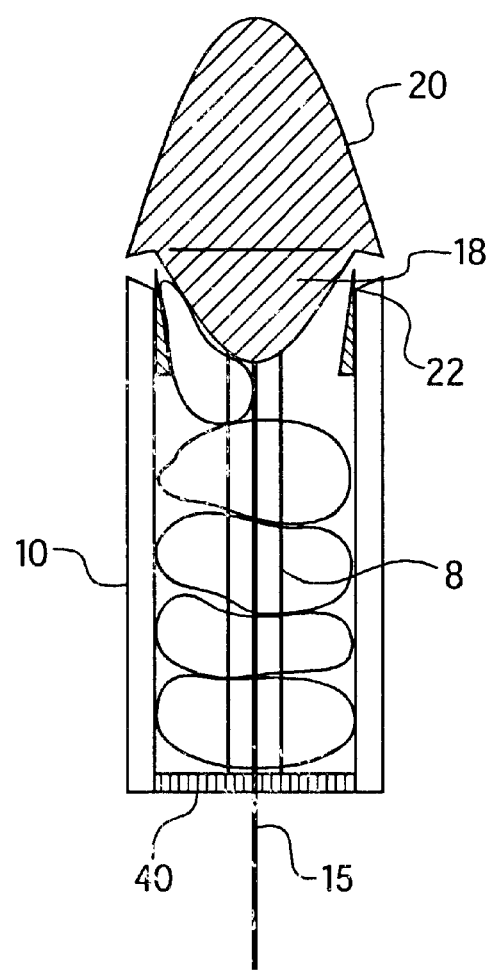
FIG. 6 shows another embodiment of the apparatus having a packing head.

FIG. 5 shows head 20' having a collapsible petal shape. This structure is advantageous for situations where there exists more rigid lesions. The petal shaped head 20' is adapted to be compressed as it slides through the lesion or blockage substance. A cone shaped head would not easily slide through such area. When head 20' is pulled back, it collects a specimen. This head structure can also be adapted to compress and thin the blockage in the lumen.

FIG. 6 shows an embodiment where blade 22 is disposed on the shaft. Packing head 18 serves to compress the collected specimens into shaft 10.

Figure 7:
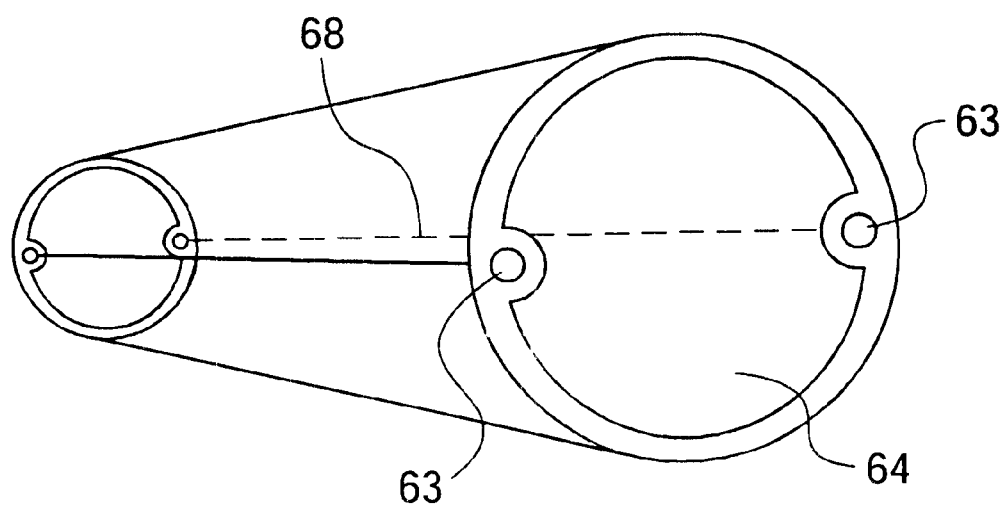
FIG. 7 a partial view of the shaft having a central lumen and two side lumens.

FIG. 7 shows an embodiment where the shaft comprises a central lumen 64 and two side lumens 63, connected by slits 68 to allow for fluid injection and sampling. This causes a suction to draw the tissue specimens into the chamber in order of acquisition.

A method of compressing the blockage, is to place different diameter heads into the lumen. The different diameter heads are placed over the wire guide allowing progressive enlargement of the lumen. After the lumen is enlarged to the diameter of the first instrument passed and that instrument removed leaving the wire guide in place, serial instruments of larger diameter are passed over the wire guide to further enlarge the lumen. Serial instrument passes allow progressive enlargement of the lumen. For example, a blood vessel or bile duct 10 mm in diameter with a 90% obstruction has a 1 mm lumen that allows passage of a 1 mm wire. Passage of a 2 mm diameter coring instrument would be followed serially by a 4 mm, then 6 mm, 8 mm and 10 mm instruments until the original lumen of 10 mm was restored. Each successive enlargement of the lumen would allow passage of a stiffer more efficient coring device followed by exchange for a stiffer wire guide to provide the necessary increase in coring force required by the larger surface area cored. Each pass traverses a path prepared by its predecessor.

Figure 2A:
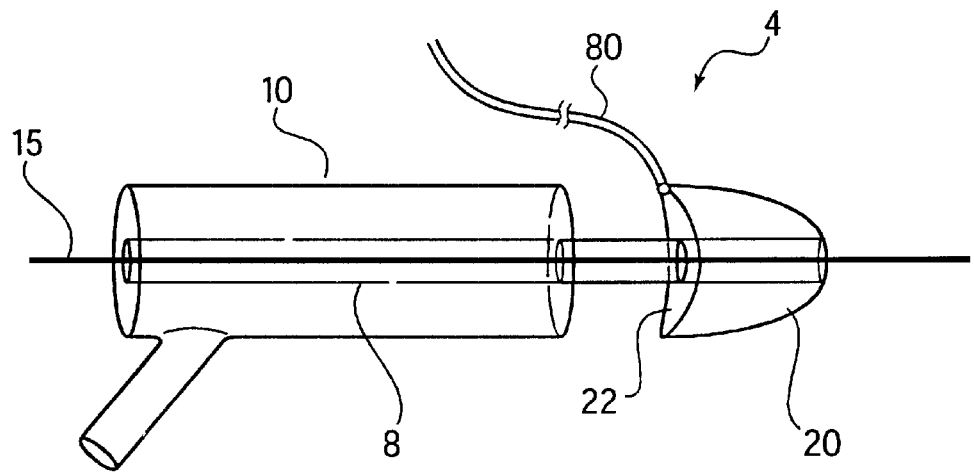
FIG. 2A shows the apparatus with a cutting blade entirely surrounding the cone head.

In another embodiment, an electrical communication 80, as shown in FIG. 2A, is supplied to the blade on the head to heat the tissue during the procedure.

Accordingly, while only a few embodiments of the present invention have been shown and described, it is obvious that many changes and modifications may be made thereunto without departing from the spirit and scope of the invention.

What is claimed is:

1. An apparatus for performing a medical procedure, comprising:
    an elongated shaft comprising an aperture extending longitudinally therethrough, said shaft having a proximal and an opposite distal end;
    an actuator tube positioned within the aperture, said actuator being hollow and having a proximal end and an opposite distal end;
    a wire guide disposed throughout the actuator tube extending from the proximal and opposite distal ends of the shaft;
    cutting means connected to the distal end of the actuator tube for cutting and collecting tissue specimens; and
    a first cap positionable over a portion of the apparatus when said portion is removed from a remaining portion of the apparatus, said first cap sealing said portion for storage of tissue specimens collected by the cutting means.

2. The apparatus according to claim 1, wherein the elongated shaft comprises a catheter and the cutting means comprises:
    a rounded cone head;
    a cutting edge attached to one of said catheter and said head; and
    a cutting surface attached to the other of said catheter and said cone head, said cutting means being actuated to cut tissue when said head is moved with respect to said catheter.

3. The apparatus according to claim 2, wherein the cone head is hollow and the first cap seals the cone head.

4. The apparatus according to claim 3, wherein the cone head has a length between 2 and 10 times the diameter of the elongated shaft.

5. The apparatus according to claim 3, wherein the cone head is perforated allowing packing of tissue specimens by fluid injection through the catheter.

6. The apparatus according to claim 2, wherein the first cap seals the catheter for retrieval and storage of captured specimens within the catheter.

7. The apparatus according to claim 6, further comprising a conical packing shaft on the cone head, said packing shaft extending into the catheter for packing, aligning and maintaining the position of collected tissue specimens within the catheter.

8. The apparatus according to claim 2, further comprising a stopper attached to the shaft at a predetermined position defining a storage compartment between the first cap and the stopper for the tissue specimens.

9. The apparatus according to claim 8, wherein the catheter is cut proximal to the stopper forming a capsule for the collected specimens.

10. The apparatus according to claim 1, wherein the wire guide is pulled from the first cap and fixed to compress the specimens within the apparatus.

11. The apparatus according to claim 1, wherein the cone head has a perforated flap that is peelably opened for removal of the tissue specimens.

12. The apparatus according to claim 1, wherein the first cap is perforated.

13. The apparatus according to claim 1, wherein the cutting means further comprises a proximally facing cone head having a cutting tool, said cutting tool being remotely deployable from said shaft, wherein said cutting tool is moveable to facilitate tissue removal.

14. The apparatus according to claim 13, wherein the shaft comprises an elongated catheter for serial acquisition and storage of specimens.

15. The apparatus according to claim 14, wherein the catheter is a plastic extrusion having a large central lumen and at least one smaller side lumens.

16. The apparatus according to claim 15, wherein said side lumens are connected via slits to said central lumen allowing fluid injection and sampling, said slits exerting suction to draw the tissue specimens into the chamber in an order of acquisition after each cutting action.

17. The apparatus according to claim 15, wherein the first cap is perforated, and the catheter is cut proximal to the chamber and sealed with the first cap.

18. The apparatus according to claim 14, further comprising a second cap for sealing the distal end of the flexible member after collection of tissue.

19. The apparatus according to claim 1, further comprising a flexible petal-shaped head for traversing a stenotic lumen to reexpand the lumen preventing down stream loss and embolization of captured tissue.

20. The apparatus according to claim 19, wherein the cutting means extends along a portion of the circumference of the head.

21. The apparatus according to claim 19, further comprising an electrical communication to the head for heating of the adjacent tissue during operation.

22. The apparatus according to claim 1, further comprising at least one lumen for fluid sampling, pressure measurement, and imaging contrast injection during operation.

23. A method for enlarging a lumen that is occluded with diseased or stenotic tissue, comprising:

inserting a device having an elongated hollow member having a cutting means into the lumen;

cutting, coring and scraping the tissue with the cutting means deployed from the elongated hollow member;

capturing the tissue within the elongated hollow member in order of collection;

removing said cutting means from the elongated member; and sealing the elongated member with at least one perforated cap, creating a processing cassette for the tissue.

24. The method according to claim 23, further comprising the steps of compressing the tissue within the elongated hollow member; and cutting the member to create a compact processing cassette.

25. A method for enlarging a lumen that is occluded with diseased or stenotic tissue, comprising:

inserting a device having an elongated hollow member and a hollow head having a cutting means into the lumen;

cutting, coring and scraping the tissue with said device;

placing the tissue within said hollow head in order of collection;

removing the hollow head from the apparatus; and sealing the hollow head with a perforated cap creating a processing cassette for the specimens.

26. The method according to claim 25, further comprising passing a series of progressively larger diameter of said devices into the lumen for coring, scraping or cutting the tissue to enlarge the lumen.

27. The method according to claim 25, wherein the hollow head blade is metal and further comprising passing an electrical current through the head.

28. The method according to claim 25, wherein the cutting means extends around only a portion of said hollow head and wherein the tissue is removed from only one side of the lumen.

29. The method according to claim 25, wherein the hollow head comprises a flexible petal-shape for traversing a stenotic lumen to reexpand the lumen.

* * * * *